United States Patent
Edelman et al.

(10) Patent No.: US 10,845,447 B2
(45) Date of Patent: Nov. 24, 2020

(54) SYSTEM AND METHOD FOR FAST INTERRUPTED STEADY-STATE (FISS) MRI

(71) Applicant: NORTHSHORE UNIVERSITY HEALTH SYSTEM, Evanston, IL (US)

(72) Inventors: Robert R. Edelman, Highland Park, IL (US); Ioannis Koktzoglou, Des Plaines, IL (US)

(73) Assignee: NORTHSHORE UNIVERSITY HEALTHSYSTEM, Evanston, IL (US)

( * ) Notice: Subject to any disclaimer, the term of this patent is extended or adjusted under 35 U.S.C. 154(b) by 139 days.

(21) Appl. No.: 16/040,730

(22) Filed: Jul. 20, 2018

(65) Prior Publication Data

US 2019/0025396 A1  Jan. 24, 2019

Related U.S. Application Data

(60) Provisional application No. 62/536,414, filed on Jul. 24, 2017.

(51) Int. Cl.
| | |
|---|---|
| *G01R 33/563* | (2006.01) |
| *G01R 33/561* | (2006.01) |
| *G01R 33/567* | (2006.01) |
| *A61B 5/0452* | (2006.01) |
| *A61B 5/055* | (2006.01) |

(Continued)

(52) U.S. Cl.
CPC ........ *G01R 33/5635* (2013.01); *A61B 5/0452* (2013.01); *A61B 5/055* (2013.01); *A61B 5/7285* (2013.01); *G01R 33/5607* (2013.01); *G01R 33/5614* (2013.01); *G01R 33/5673* (2013.01); *G01R 33/56509* (2013.01); *G01R 33/4824* (2013.01)

(58) Field of Classification Search
CPC .......... G01R 33/5635; G01R 33/56509; G01R 33/5614; G01R 33/5673; G01R 33/5607; G01R 33/4824; A61B 5/0452; A61B 5/055; A61B 5/7285
See application file for complete search history.

(56) References Cited

U.S. PATENT DOCUMENTS

| | | | |
|---|---|---|---|
| 7,253,620 B1 | 8/2007 | Derbyshire | |
| 8,332,010 B2 | 12/2012 | Edelman | |

(Continued)

OTHER PUBLICATIONS

Han et al., "Ultrafast 3D spin-echo acquisition improves Gadolinium-enhanced MRI signal contrast enhancement" (Year: 2014).*

(Continued)

*Primary Examiner* — Tung X Nguyen
*Assistant Examiner* — Feba Pothen
(74) *Attorney, Agent, or Firm* — Quarles & Brady LLP (57) ABSTRACT

A system and method for controlling a magnetic resonance imaging (MRI) system to create magnetic resonance (MR) angiograms of a subject. The method includes controlling the MRI system to acquire MR data by performing a pulse sequence that includes at least one set of modules formed by a first α/2 module, a (readout, α)n module, a second α/2 module. In this case, α denotes a radiofrequency (RF) flip angle and n denotes a number of times that the set of modules is repeated. The method also includes reconstructing an MR angiogram of the subject from the MR data.

35 Claims, 5 Drawing Sheets

(51) Int. Cl.
    *A61B 5/00*     (2006.01)
    *G01R 33/56*     (2006.01)
    *G01R 33/565*     (2006.01)
    *G01R 33/48*     (2006.01)

(56) References Cited

U.S. PATENT DOCUMENTS

| | | | |
|---|---|---|---|
| 9,211,081 B2 | 12/2015 | Edelman | |
| 2011/0166436 A1* | 7/2011 | Edelman | G01R 33/5614 600/410 |
| 2014/0200435 A1* | 7/2014 | Edelman | A61B 5/055 600/410 |
| 2016/0338600 A1* | 11/2016 | Edelman | A61B 5/0263 |

OTHER PUBLICATIONS

Carr, H. Y. "Steady-state free precession in nuclear magnetic resonance." Physical Review 112.5 (1958): 1693.
Derbyshire, J. A., et al. "S5FP: spectrally selective suppression with steady state free precession." Magnetic Resonance in Medicine: An Official Journal of the International Society for Magnetic Resonance in Medicine 54.4 (2005): 918-928.
Haase, A., et al. J Magn Reson 67 (1986): 258-266.
Marckmann, P. et al., "Nephrogenic Systemic Fibrosis: Suspected Causative Role of Gadodiamide Used for Contrast-Enhanced Magnetic Resonance Imaging," J. Am. Soc. Nephrol., 2006; 17 (9):2359-2362.
Scheffler, K., et al. "Magnetization preparation during the steady state: fat-saturated 3D TrueFISP." Magnetic Resonance in Medicine: An Official Journal of the International Society for Magnetic Resonance in Medicine 45.6 (2001): 1075-1080.

\* cited by examiner

SYSTEM AND METHOD FOR FAST INTERRUPTED STEADY-STATE (FISS) MRI

CROSS-REFERENCE TO RELATED APPLICATIONS

The present disclosure is based on, claims priority to, and incorporates herein by reference in its entirety for all purposes, U.S. Provisional Patent Application Ser. No. 62/536,414, filed Jul. 24, 2017, and entitled, "SYSTEM AND METHOD FOR FAST INTERRUPTED STEADY-STATE (FISS) MRI."

STATEMENT REGARDING FEDERALLY SPONSORED RESEARCH

This invention was made with government support under 1R01HL130093 and R21HL126015 both awarded by the National Institutes of Health. The government has certain rights in the invention.

BACKGROUND

The present disclosure relates to magnetic resonance imaging (MRI) and systems. More particularly, the present disclosure relates to systems and methods for magnetic resonance angiography (MRA).

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients $G_x$, $G_y$, and $G_z$ are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

Magnetic resonance angiography (MRA) uses the magnetic resonance phenomenon to produce images of the human vasculature. To enhance the diagnostic capability of MRA, a contrast agent such as gadolinium can be injected into the patient prior to the MRA scan. The goal of this contrast enhanced (CE) MRA method is to acquire the central k-space views at the moment the bolus of contrast agent is flowing through the vasculature of interest in order to benefit from improved contrast. That is, collection of the central lines of k-space during peak arterial enhancement, therefore, is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins.

Recently, a rare and serious pathology involving fibrosis of skin, joints, eyes, and internal organs referred to as nephrogenic systemic fibrosis ("NSF") has been correlated to the administration of gadolinium-based contrast agents to patients undergoing contrast-enhanced MRA studies. The link between gadolinium-based contrast agents and NSF is described, for example, by P. Marckmann, et al., in "Nephrogenic Systemic Fibrosis: Suspected Causative Role of Gadodiamide Used for Contrast-Enhanced Magnetic Resonance Imaging," *J. Am. Soc. Nephrol.,* 2006; 17 (9):2359-2362. As a result of the increased incidence of NSF, methods for MRA that do not rely on the administration of a contrast agent to the patient have become an important field of research. However, current methods for non-contrast angiography are limited in their utility One of the most commonly used pulse sequence in cardiovascular imaging is balanced steady-state free-precession ("bSSFP"), also called trueFISP. The bSSFP pulse sequence is a highly efficient imaging technique that can be used to produce high signal from flowing blood, as well as from fluid-containing structures and fat. It is routinely used for cine and delayed enhanced imaging of the heart.

Despite its clinical utility, the bSSFP pulse sequence has a major drawback for cardiovascular imaging due to sensitivity to artifacts from blood flow. These flow artifacts are especially severe with rapid systolic blood flow and near arterial stenosis and in regions of B0 inhomogeneity. Out of slice magnetization can also produce flow artifacts with bSSFP, especially in areas of off-resonance.

Other drawbacks of bSSFP include: (1) persistent signal contributions from vascular spins that have flowed out of the slice, resulting in flow artifacts and degrading the quality of MR angiograms; (2) difficulty in achieving effective fat suppression with long echo trains or with a radial k-space trajectory; (3) high power deposition, due to the rapid sequential application of radiofrequency (RF) pulses using a large flip angle; and (4) sensitivity to off-resonance artifacts, caused by static magnetic field inhomogeneity.

Despite its great utility at 1.5 Tesla, the use of the bSSFP pulse sequence at high field is severely curtailed by these drawbacks. For example, off-resonance and flow artifacts are much worse at high field, to the point that the images become of a quality that is not viable for diagnostics.

One alternative is to use a spoiled gradient-echo pulse sequence, also called fast low angle shot (FLASH). The FLASH pulse sequence is much less sensitive to off-resonance and flow artifacts, and power deposition is much less of an issue because relatively small flip angles are used. However, the FLASH pulse sequence has its own drawbacks, which include: (1) inferior SNR when compared to the bSSFP pulse sequence and (2) flow saturation artifacts for vascular spins that move slowly or remain in-plane over extended distances.

Variations of the bSSFP pulse sequence have been developed in which the echo train is intermittently paused and restarted to improve fat suppression. For instance, Scheffler et al., as described in Scheffler K, Heid O, Hennig J. Magnetization preparation during the steady state: fat saturated 3D TrueFISP. Magn Reson Med 2001; 45(6):1075-1080, broke up lengthy bSSFP echo trains with pairs of store/restore alpha/2 RF pulses (at a rate of ≈5-6 Hz) to allow the repeated application of fat saturation RF pulses.

Derbyshire et al., as described in Derbyshire J A, Herzka D A, McVeigh E R. SSFP: spectrally selective suppression with steady state free precession. Magn Reson Med 2005; 54(4):918-928; U.S. Pat. No. 7,253,620, Aug. 7, 2007, describes another variant of interrupted bSSFP called "spectrally selective suppression with SSFP" (S5FP), which uses the bandpass filtering properties of interrupted bSSFP to suppress fat signal. The method acquires a series of Cartesian bSSFP echo trains that are each sandwiched between tailored opening and closing subsequences of RF pulses and gradients, with each series repeating at a rate of ≈10 Hz. In other configurations, this rate could be approximately 10-20 Hz. This work, however, has not gained clinical traction, in part due to the resulting artifacts. In particular, severe ghost artifacts occur in the phase-encoding direction due to mismatched echo intensities that arise from repeated interruptions of the bSSFP echo train. The use of a Cartesian k-space trajectory with SSFP directly contributes to the ghost artifacts, since periodic signal fluctuations that occur during the acquisition of central k-space lines have a disproportionately large impact on image contrast. As a result, with S5FP, a complex process of data scaling is used during the image reconstruction process to reduce the ghost artifacts.

The techniques described by Scheffler et al. and Derbyshire et al. provide efficient fat suppression. However, when applied in the context of angiography, the resulting images further suffer from flow artifacts. As described above, flow artifacts may include, for example, steady-state magnetization from out-of-slice spins as well as strongly oscillating signals from off-resonant spins in the transient-state that occur using a bSSFP readout. With bSSFP, these unwanted sources of MR signal variation carry over from one repetition to the next. Consequently, the echo train lengths of Scheffler et al. and Derbyshire et al. (e.g. 24 or more echoes per train) suffer from substantial flow artifacts that are encountered with bSSFP.

It would therefore be desirable to provide a method for MRA that is not susceptible to these drawbacks with the pulse sequences that are currently available to clinicians for MRA.

SUMMARY

The present disclosure provides systems and methods that overcome the aforementioned drawbacks using a pulse sequence that provides excellent signal-to-noise ratio (SNR) and image contrast, while avoiding the above-described drawbacks of bSSFP techniques. The systems and methods of the present disclosure may be referred to as the radial fast interrupted steady-state (FISS) technique and provides high on-resonant signal of bSSFP-based imaging, while reducing flow artifacts and signal fluctuations associated with off-resonant spins and spins that have exited the imaging slice. Furthermore, the FISS technique reduces saturation artifacts that are observed with FLASH imaging.

In accordance with aspects of the present disclosure, a method for controlling a magnetic resonance imaging (MRI) system to create magnetic resonance (MR) angiograms of a subject. The method includes controlling the MRI system to acquire MR data by performing a gradient echo pulse sequence at a rate greater than 20 Hz when imaging without a MR contrast agent, and greater than 10 Hz when imaging with a MRI contrast agent, the gradient echo pulse sequence including at least one set of modules formed by a first $\alpha/2$ module, a (readout, $\alpha$)n module, and a second $\alpha/2$ module. In this case, $\alpha$ denotes a radiofrequency (RF) flip angle and n denotes a number of times that the set of modules is repeated, and n ranges from 1 to 10 when imaging without a MRI contrast agent, and n ranges from 1 to 32 when imaging with a MRI contrast agent. The method also includes generating a readout of the (readout, $\alpha$)n module using a radial k-space trajectory, and reconstructing an MR angiogram of the subject from the MR data.

In accordance with another aspect of the disclosure, a magnetic resonance imaging (MRI) system is provided that includes a magnet system configured to generate a polarizing magnetic field about at least a portion of a subject arranged in the MRI system and a plurality of gradient coils configured to apply a gradient field to the polarizing magnetic field. The system also includes a radio frequency (RF) system configured to apply an excitation field to the subject and acquire MR image data from a ROI and a computer system. The computer system is programmed to control the plurality of gradient coils and the RF system to acquire MR data by performing a gradient echo pulse sequence at a rate greater than 20 Hz, the gradient echo pulse sequence including at least one set of modules formed by a first $\alpha/2$ module, a (readout, $\alpha$)n module, and a second $\alpha/2$ module. In this case, $\alpha$ denotes a radiofrequency (RF) flip angle and n denotes a number of times that the set of modules is repeated, and n ranges from 1 to 10 when imaging without a MRI contrast agent, and n ranges from 1 to 32 when imaging with a MRI contrast agent. The computer system is also programmed to generate a readout of the (readout, $\alpha$)n module using a radial k-space trajectory, and reconstruct an MR angiogram of the subject from the MR data.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
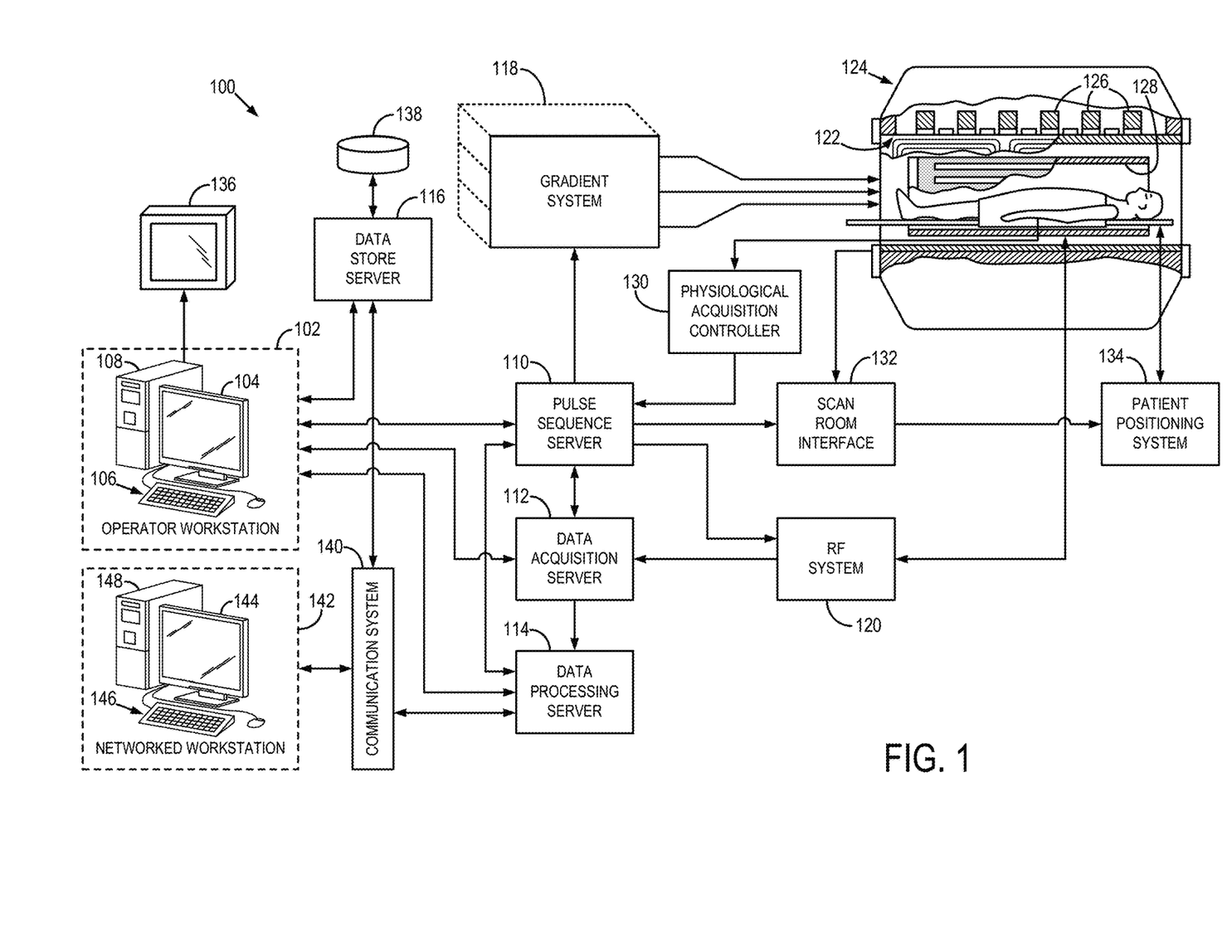
FIG. 1 is a block diagram of an example MRI system for use in accordance with aspects of the present disclosure.

Referring now to FIG. 1, the above-described systems and methods may be implemented using or designed to accompany a magnetic resonance imaging ("MRI") system 100, such as is illustrated in FIG. 1. The MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2}$$ Eqn. 1;

and the phase of the received magnetic resonance signal may also be determined according to the following relationship:

$$\varphi = \tan^{-1}\left(\frac{Q}{I}\right).$$ Eqn. 2

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction techniques, such as iterative or backprojection reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 112 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchange between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2:
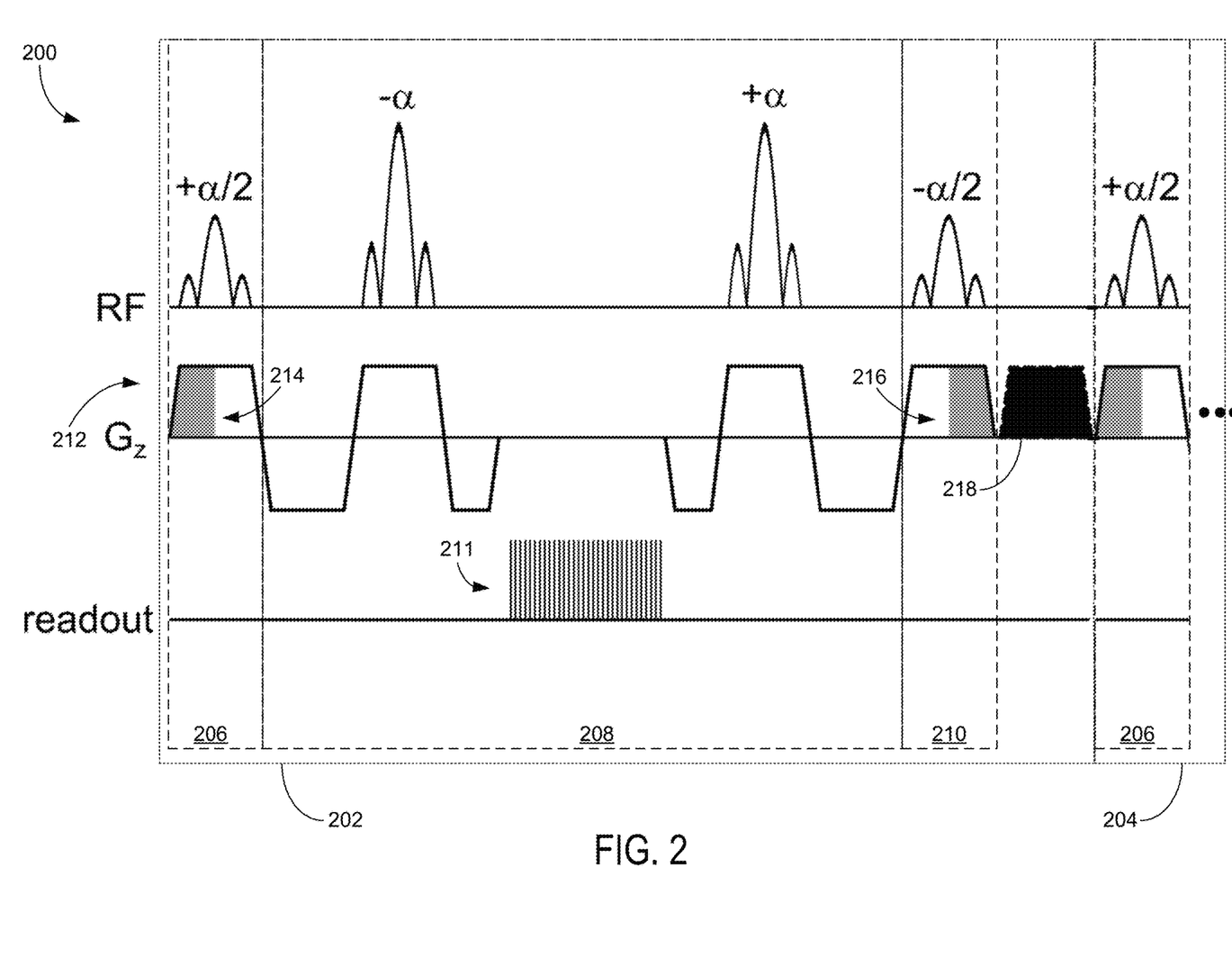
FIG. 2 is a pictorial representation of a pulse sequence performed by the MRI system of FIG. 1 in accordance with the present disclosure. Gradient activity in the phase-encoding and readout-encoding axes are not shown.

Referring now to FIG. 2, a pulse sequence 200 is provided that is one example of an implementation of the radial fast interrupted steady-state (FISS) pulse sequence or technique as provided in the present disclosure. The FISS technique may be used to suppress flow and off-resonance artifacts that are encountered with previously-described steady-state imaging techniques. As will be described, the pulse sequence 200 may generally be of the form of a gradient-echo pulse sequence. In the illustrated, non-limiting example, gradient activity in the phase-encoding and read-out-encoding axes are not shown, but would be readily understood by one of ordinary skill in the art as being generally consistent with a gradient-echo pulse sequence. The pulse sequence 200 includes a series of FISS modules 202, 204 that are formed from an α/2 pulse module 206, a (readout, α)n module 208, an α/2 pulse module 210 giving rise to a readout 211, where α denotes the radiofrequency flip angle, n denotes the number of repetitions, and the phases of applied a and α/2 RF pulses alternate. As illustrated, the phases of applied a and α/2 RF pulses alternate. In one non-limiting example, n is selected to allow control of flow artifacts. For example, n may be selected to ranges between 1 and 10 repetitions or 1 and 7 repetitions when imaging without a MRI contrast agent, and 1 to 32 when imaging with a MRI contrast agent. In another non-limiting example, n is at least 1 and less than one-half the number of views that are acquired using the pulse sequence 200. The readout of the (readout, α)n module 208 may use a radial sampling of k-space. In some aspects, data is be collected using radial sampling of k-space with a trajectory in which radial views are distributed across an azimuthal angle of at least 540 degrees. In some aspects, an offset frequency is varied across the radial views.

In a manner analogous to bSSFP pulse sequence, the FISS pulse sequence of this example pulse sequence 200 uses balanced gradients 212. However, akin to spoiled gradient-echo imaging pulse sequence, the unbalanced gradient areas 214, 216 are applied in the slice-select direction ($G_z$) near the α/2. An optional spoiler gradient 218 may be applied between FISS pulse modules 202, 204 to further spoil residual transverse magnetization. In addition, the pulse sequence 200 may include a magnetization preparation targeted to fat suppression or magnetization transfer that precedes the FISS modules 202, 204. In addition, the phases of the applied RF pulses may be varied between modules to further spoil residual transverse magnetization.

The use of α/2 pulses in the respective modules 206, 210 interrupts (i.e. stops and starts) the bSSFP echo train (±α) and stores the on-resonance spectral band along z as longitudinal magnetization using the ±α/2 pulse. Simultaneously, off-resonance spectral bands can be suppressed by balanced gradients 212 and the spoiler gradient 218. In some aspects, the α/2 pulses in the respective modules 206, 210 may be applied to interrupt the bSSFP echo train at a rate greater than, as a non-limiting example, 20 Hz. In some aspects, the rate could be 30 Hz. In other aspects, the rate ranges between 50 and 100 Hz. Interrupting the bSSFP echo train at these higher frequencies was found to significantly reduce flow artifacts when compared with conventional bSSFP techniques.

The pulse sequence 200 may include flow-sensitizing or velocity encoding gradients to acquire the MR data from the subject with flow- or phase-encoding. To form a flow-sensitive, phase contrast image, multiple datasets are acquired with differing flow-sensitizing gradients applied (e.g., one with and one without flow-sensitizing gradients) to create two different image sets that are subtracted to form MR angiograms of the subject that illustrate flow.

The FISS technique 200, which spoils residual traverse magnetization between one FISS module to the next, markedly reduces flow artifacts characteristic of conventional bSSFP imaging and offers advantages over previously described techniques. In some aspects, using a low number of repetitions, n (e.g. 1 to 10), provides benefits by suppressing steady-state magnetization from out-of-slice spins as well as strongly oscillating signals from off-resonant spins in the transient-state that begin to accumulate with a higher number of repetitions. Thus, the number of repetitions can be selected to control against the generation of undesirable flow artifacts.

In some aspects, using a radial k-space trajectory offers improvements over a Cartesian k-space trajectory. In some aspects, when multiple bSSFP readouts are collected (i.e. n>1), radial sampling is less sensitive than Cartesian sampling to artifacts caused by mild signal fluctuations arising from the interrupted nature of the FISS module. With Cartesian k-space sampling, these signal fluctuations produce ghost artifacts in the phase-encoding direction. Conversely, these small signal variations produce minimal to no apparent artifacts with radial sampling. By distributing the signal fluctuations over a large (>540 degrees) azimuthal range of radial views, FISS is highly effective at minimizing image artifacts due to the signal fluctuations. In other aspects, due to oversampling of central k-space, radial sampling is less sensitive than Cartesian sampling to motion and arterial pulsation artifacts.

Also, the above-described acquisitions may be paired with accelerated imaging techniques, such as radial under sampling, compressed sensing, or simultaneous multi-slice acquisitions, to further accelerate the data acquisition.

Figure 3A:
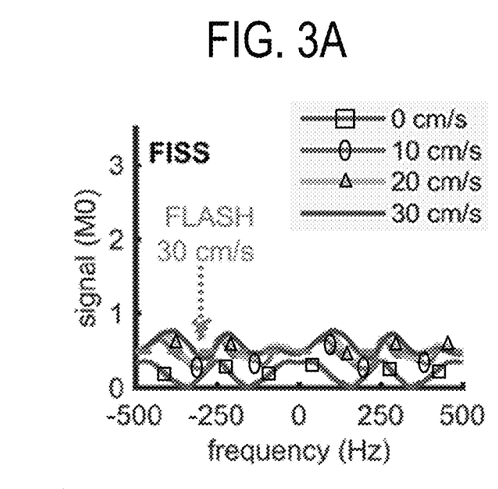
FIG. 3A is a graph showing steady-state transverse magnetization of FISS as a function of off-resonance frequency for arterial blood imaged at 3.0 T using a TR=4 ms.
Figure 3B:
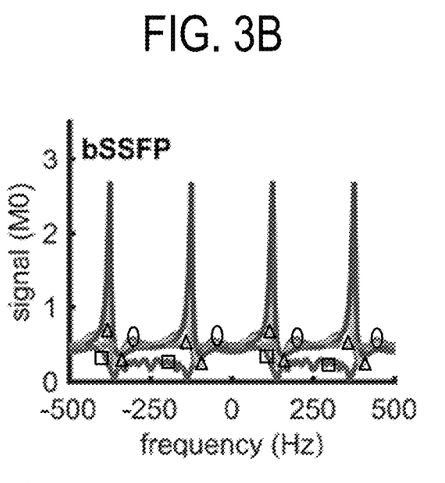
FIG. 3B is a graph similar to FIG. 3A, but created using a bSSFP pulse sequence.
Figure 3C:
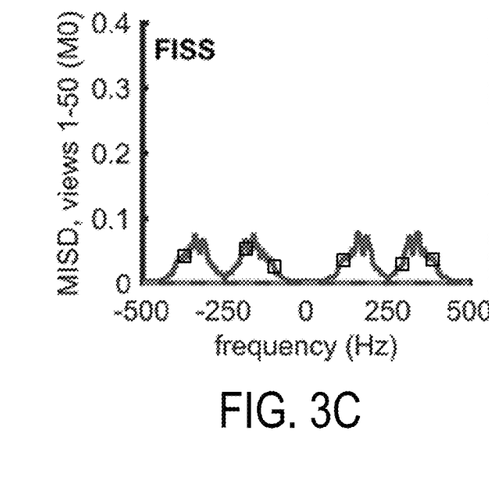
FIG. 3C is a graph showing the median inter-readout complex signal differences (MISD) over the first 50 readouts for FISS.
Figure 3D:
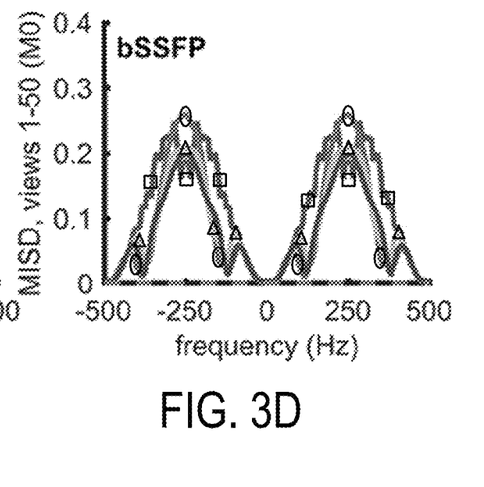
FIG. 3D is a graph similar to FIG. 3C, but created suing a bSSFP pulse sequence.

For example, phantom studies showed that the FISS technique described with respect to FIG. 2 retains the high SNR of bSSFP. Specifically, contrast achieved using the above-described FISS pulse sequence, when compared with images acquired using FLASH and bSSFP in a phantom containing eight dilutions of gadopentetate dimeglumine, clearly showed that FISS provides a contrast that is distinct from FLASH. Also, the FISS technique provides greater suppression of off-resonant spins with respect to bSSFP, as illustrated in FIGS. 3 A-D. As shown in FIGS. 3A-B, bSSFP demonstrates an approximate 5 fold increase in signal from out-of-slice magnetization near the off-resonant frequencies of ±0.5/TR and ±1.5/TR (±125 Hz and ±375 Hz for TR=4 ms), FISS avoids this phenomenon and provides a more uniform signal spectrum. As used herein, TR may be defined as the spacing between α and −α RF pulses. Relevant to the imaging of flow in areas of off-resonance, the notches of suppressed off-resonance frequencies that are predicted for FISS imaging of stationary spins are eliminated for flowing spins. FISS also considerably reduces the median inter-readout complex signal differences (MISD) over the first 50 readouts as compared with bSSFP, as shown in FIGS. 3C-D.

The FISS pulse sequence described with respect to FIG. 2 can also be combined with other imaging techniques. In one non-limiting example, the FISS technique can be combined with cine imaging to reduce out-of-slice flow artifacts that often affect cine bSSFP. Using conventional bSSFP, interrupting the steady-state to apply a magnetization preparation module results in saturation of flowing spins as well as severe image artifacts. However, FISS allows for a reduction in flow artifacts along with the ability to interrupt the steady-state data acquisition without resulting image artifacts. Thus, the FISS technique can be combined with a magnetization preparation module and RF tagging techniques to measure blood flow and tissue properties such as tissue strain. In some aspects, the magnetization preparation module includes spatial saturation, spatial modulation of magnetization (SPAMM), fat suppression, diffusion, and magnetization transfer modules. In some aspects, signal intensity of background tissues may be reduced by acquiring at least two sets of MR data using at least a first magnetization preparation module and a second magnetization preparation module, and computing a difference between the at least two sets of MR data.

Additionally, the FISS technique can be used as a readout for pulse sequences performing time-of-flight studies or utilizing the "quiescent interval" (QI), such as the quiescent interval steady-state (QISS) and those described in co-pending patent application Ser. Nos. 12/574,856 and 13/026,482, which are incorporated herein by reference in its entirety, and the like. The FISS technique described above may be particularly useful as a readout for use with the QISS MRA technique at 3 Tesla. Studies of a QISS-FISS implementation showed greatly improved image quality compared with both bSSFP and FLASH readouts.

Figure 4:
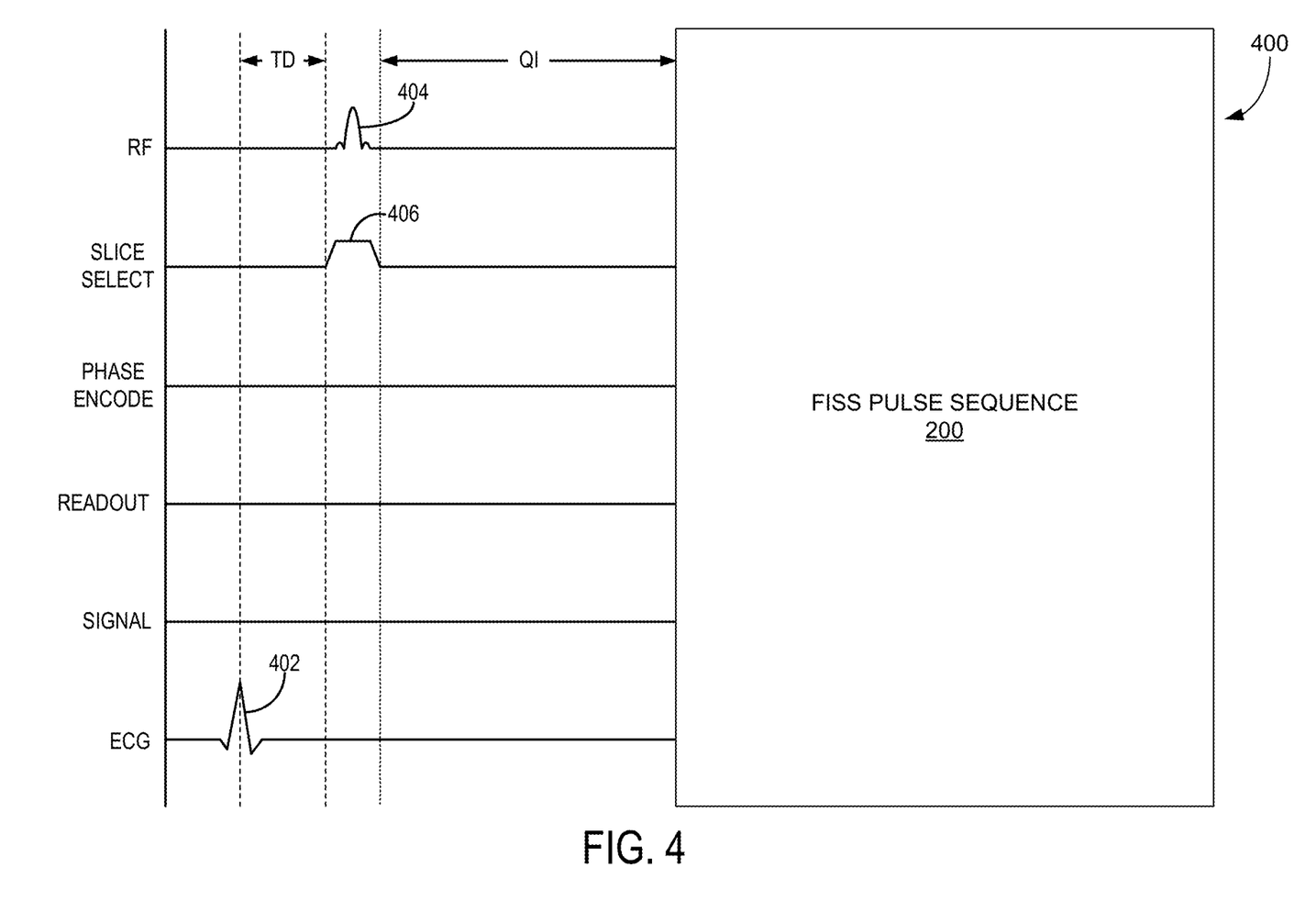
FIG. 4 is a pictorial representation of a QISS-FISS pulse sequence in accordance with the present disclosure.

Specifically, referring now particularly to FIG. 4, an example of a pulse sequence using a QI and, in particular, the QISS pulse sequence is illustrated 400 utilizing a FISS pulse sequence readout 200. The QISS pulse sequence 400 is cardiac gated, such that the acquisition of k-space data is timed with respect to the flow of arterial blood. Specifically, the pulse sequence 400 is timed to be played out with respect to the peak of the R-wave 402 in a concurrently acquired echocardiogram ("ECG"). It should be appreciated by those skilled in the art, however, that other methods for cardiac synchronization of the following pulse than relying on an ECG signal are possible. For example, cardiac synchronization can be achieved using self-gating techniques that rely on measurement of flow signal or phase. Once the trigger 402 is reached, a slice-selective RF saturation pulse 404 is first played out in the presence of a slice-selective gradient 406. The application of this slice-selective RF saturation pulse 404 has the effect of suppressing the signals from background tissues as well as those venous spins that are present in the prescribed slice. The flip angle for this slice-selective RF saturation pulse 404 may be about 90 degrees; however, larger or smaller flip angles may be desirable in some circumstances. The slice-selective RF saturation pulse 404 is timed to occur at a preset time delay (TD) after the occurrence of the R-wave 402. For example, TD may be set to 100 ms.

The duration of time that is allowed to pass after the application of the slice-selective RF saturation pulse 404 is herein referred to as the "quiescent interval" ("QI"). This duration of time is specifically tailored to coincide with the rapid inflow of arterial blood into a prescribed imaging slice, and so that the zero line of k-space is acquired during the slow, diastolic inflow of arterial blood into the imaging slice. More particularly, a central portion of k-space is sampled during the slow, diastolic inflow of arterial blood into the imaging slice before the peripheral regions of k-space are sampled. The result of this is a substantial suppression of flow-based image artifacts. Put another way, this provides a method that is substantially insensitive to flow velocities in the prescribed image slice. Moreover, the QI allows for a maximal inflow of unsaturated arterial spins into the imaging slice, such that an improved discrimination of arterial spins is provided in the resultant images. This is even so when the patient's vasculature is significantly impacted by vascular diseases such as peripheral vascular disease ("PVD"). Exemplary values of QI in this configuration of the pulse sequence are on the order of 260 ms.

After the QI has passed, the pulse sequence proceeds with data acquisition, which is accomplished, in this application, using the FISS pulse sequence described above with respect to FIG. 2.

Figure 5:
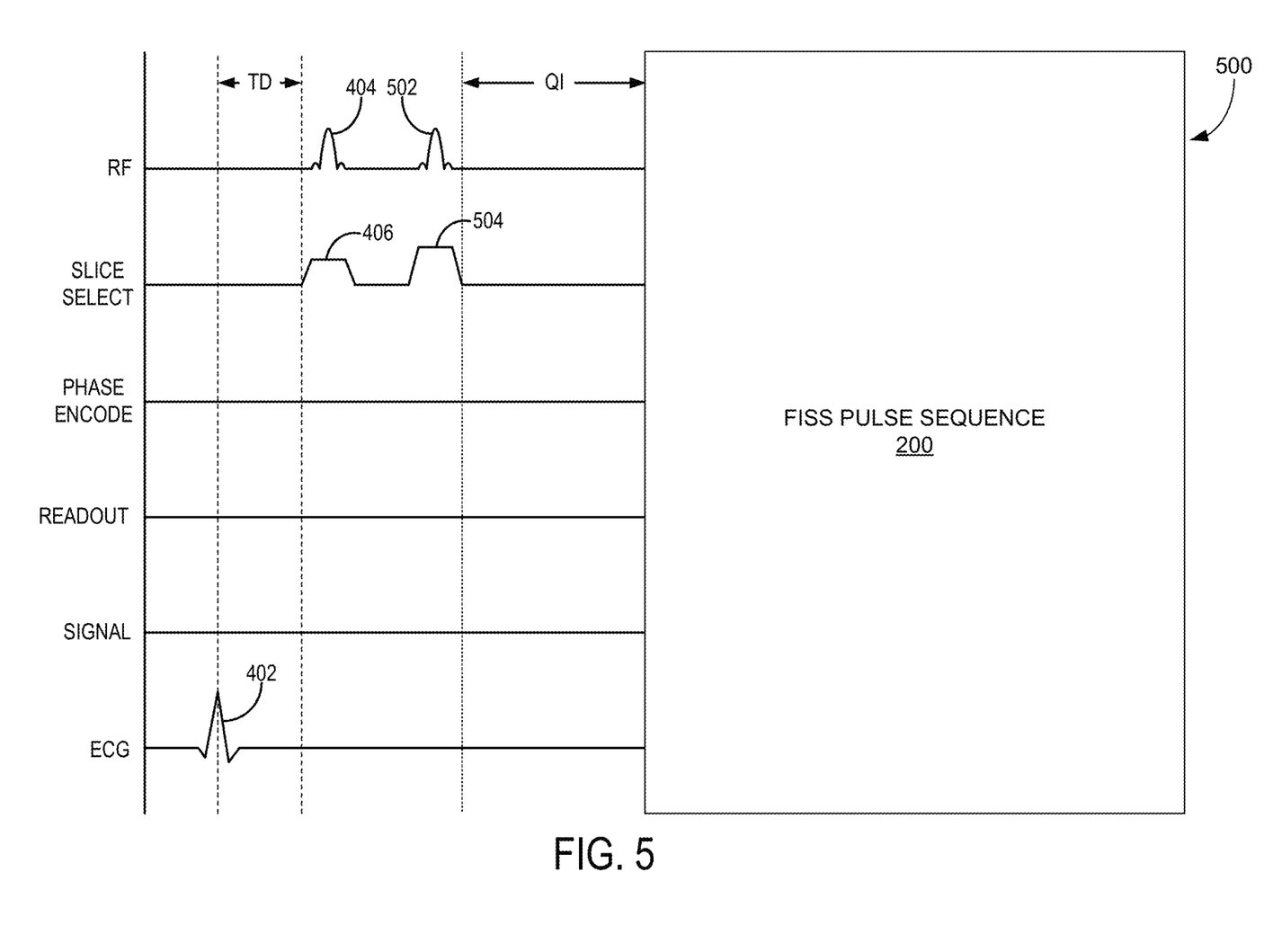
FIG. 5 is a pictorial representation of another QISS-FISS pulse sequence in accordance with the present disclosure.

Referring now to FIG. 5, another configuration of the QISS-FISS pulse sequence 500 is pictorially shown. This pulse sequence 500 is also cardiac gated, such that the acquisition of k-space data is timed with respect to the flow of arterial blood. Specifically, the pulse sequence is timed to be played out with respect to the peak of the R-wave 402 in a concurrently acquired echocardiogram ("ECG"). However, the data acquisition portion of the pulse sequence 500 is preceded by the application of multiple RF saturation pulses 404, 502. By employing RF saturation pulses 404, 502 instead of inversion recovery pulses, the longitudinal magnetization is always reset to zero prior to the beginning of the QI. This is not necessarily the case when employing inversion recovery-based methods, as residual longitudinal magnetization resulting from inadequate inversion may confound the subsequently detected MR signals. Moreover, by always resetting the longitudinal magnetization of the slice to zero, the use of a slice-selective RF saturation pulse ensures that the tissue signal remains substantially uniform across different slices despite variations in the R-R interval due to cardiac arrhythmias. This is not the case with inversion-recovery based methods.

First, a slice-selective RF saturation pulse 404 is played out in the presence of the slice-selective gradient 406. The application of this slice-selective RF saturation pulse 404 has the effect of suppressing the signals from background tissues as well as those venous spins that are present in the prescribed slice. The slice-selective RF saturation pulse 404 is timed to occur at the preset TD after the occurrence of the R-wave 402. For example, again, the TD may be set to 100 ms.

To suppress signals from venous spins that will flow into the prescribed slice, a second, slab-selective RF saturation pulse 502 is played out in the presence of a slab-selective gradient 504. The slab-selective RF saturation pulse 502 has the effect of suppressing venous signals in a slab that is contiguous with the prescribed imaging slice. Specifically, when imaging the peripheral arteries, the prescribed slab is chosen to be caudal to, and contiguous with, the prescribed imaging slice such that saturated venous blood flows into the imaging slice in the caudal-cranial direction while unsaturated arterial spins flow into the imaging slice in the cranial-caudal direction. Similarly, when imaging, for example, the carotid artery, the prescribed slab is chosen to be cranial to, and contiguous with, the prescribed imaging slice such that saturated venous blood flows into the imaging slice in the cranial-caudal direction while unsaturated arterial spins flow into the imaging slice in the caudal-cranial direction. Exemplary RF excitation slab thicknesses are on the order of 150 mm; however, it will be appreciated by those skilled in the art that other thicknesses can be selected depending on the intended application and subject at hand. It will also be appreciated that in some circumstances it may be desirable to shift the RF excitation slab so that it is not contiguous with the imaging slice.

In this alternate configuration of the pulse sequence, the QI is defined as the duration of time occurring after the application of the slab-selective RF saturation pulse 502 and before the FISS pulse sequence 200 is used to perform readout. Like the previously described QI, however, this duration of time is specifically tailored so that the zero line of k-space is acquired during the slow, diastolic inflow of arterial blood into the prescribed imaging slice. As described above, the result of allowing the QI to pass before data acquisition is a substantial suppression of flow-based image artifacts. Put another way, this provides a method that is substantially insensitive to flow velocities in the prescribed image slice. Exemplary values of QI in this configuration of the pulse sequence are on the order of 250 ms.

A comparison of axial QISS images through the heart using various readouts at 3 Tesla showed that QISS-bSSFP with flip angle of 30 degrees suffered from a signal hotspot with severe anatomic distortion at the medial margin of the heart, due to a combination of off-resonance and out-of-slice flow effects. However, at the same flip angle, QISS-FISS showed excellent flow contrast without significant artifacts. At a flip angle of 89 degrees, QISS-FLASH showed severe image degradation. At the same flip angle, QISS-FISS showed excellent image quality, without the issues present in the QISS-FLASH images.

It is to be appreciated by those skilled in the art, however, that other methods for gating and synchronization techniques may be used with the FISS pulse sequence 200. In one non-limiting example, respiratory gating and synchronization may be used in combination with the FISS pulse sequence 200. Additionally, motion reduction techniques such as navigator gating, and motion correction techniques to align a series of sequentially acquired images may be used in combination with the FISS pulse sequence 200. Gating and synchronization techniques may be used in combination with the FISS pulse sequence 200.

The present invention has been described in terms of one or more preferred embodiments, and it should be appreciated that many equivalents, alternatives, variations, and modifications, aside from those expressly stated, are possible and within the scope of the invention.

We claim:

1. A method for controlling a magnetic resonance imaging (MRI) system to create magnetic resonance (MR) angiograms of a subject, the method including steps comprising:

(a) controlling the MRI system to acquire MR data by performing a gradient-echo pulse sequence at a rate greater than 20 Hz when the subject is free of any MRI contrast agent, and at a rate greater than 10 Hz when the subject has received a dose of the MM contrast agent, the gradient-echo pulse sequence including at least one set of modules formed by a first $\alpha/2$ module, a (readout, $\alpha$)n module, a second $\alpha/2$ module, and a spoiler gradient module, wherein $\alpha$ denotes a radiofrequency (RF) flip angle, n denotes a number of times that the set of modules is repeated, and n ranges from 1 to 10 when the subject is free of the MRI contrast agent and n ranges from 1 to 32 when the subject has received the dose of the MRI contrast agent;

(b) performing a readout using the (readout, a)n module and a radial k-space trajectory;

(c) reconstructing an MR angiogram of the subject from the MR data.

2. The method of claim 1 wherein the rate greater than 20 Hz ranges from 50 to 100 Hz.

3. The method of claim 1 wherein the radial k-space trajectory comprises radial views that are distributed across an azimuthal angle of at least 540 degrees.

4. The method of claim 3 wherein an offset frequency is varied across the radial views.

5. The method of claim 1 wherein a phase of a RF pulses and $\alpha/2$ RF pulses in the first and second $\alpha/2$ modules and the (readout, $\alpha$)n module alternate.

6. The method of claim 1 wherein the spoiler gradient module is integrated with one of the first or second $\alpha/2$ module or the (readout, $\alpha$)n module.

7. The method of claim 1 wherein the spoiler gradient module is integrated between one of the first or second $\alpha/2$ module or the (readout, $\alpha$)n module.

8. The method of claim 1 wherein the MR data is at least one of two-dimensional (2D) MR data, three-dimensional (3D) data, or cine MR data.

9. The method of claim 1 wherein the MR angiogram includes a bright vascular signal.

10. The method of claim 1 wherein the set of modules forms a readout for a time-of-flight MR angiography or a quiescent interval steady-state (QISS) angiography pulse sequence.

11. The method of claim 1 wherein the gradient-echo pulse sequence further includes a magnetization preparation module including a spatial saturation, spatial modulation of magnetization (SPAMM), fat suppression, diffusion, or magnetization transfer module.

12. The method of claim 1 wherein the pulse sequence is accelerated using radial undersampling, compressed sensing, or simultaneous multi-slice techniques.

13. The method of claim 1 wherein acquiring the MR data further includes synchronizing acquisition to a cardiac cycle or a respiratory cycle.

14. The method of claim 1 wherein acquiring the MR data further includes performing a motion reduction technique including navigator gating.

15. The method of claim 1 wherein the gradient-echo pulse sequence is performed before, during, or after the injection of the MRI contrast agent.

16. The method of claim 1 wherein acquiring the MR data further includes performing a motion correction technique to align a plurality of sequentially acquired images.

17. A magnetic resonance imaging (MM) system comprising:

a magnet system configured to generate a polarizing magnetic field about at least a portion of a subject arranged in the MM system;

a plurality of gradient coils configured to apply a gradient field to the polarizing magnetic field;

a radio frequency (RF) system configured to apply an excitation field to the subject and acquire MR image data from a region of interest;

a computer system programmed to:
(a) control the MM system to acquire MR data by performing a gradient-echo pulse sequence at a rate greater than 20 Hz when the subject is free of any MM contrast agent, and at a rate greater than 10 Hz when the subject has received a dose of the MRI contrast agent, the gradient-echo pulse sequence including at least one set of modules formed by a first $\alpha/2$ module, a (readout, $\alpha$)n module, a second $\alpha/2$ module, and a spoiler gradient module, wherein $\alpha$ denotes a radiofrequency (RF) flip angle, n denotes a number of times that the set of modules is repeated, and n ranges from 1 to 10 when the subject is free of the MM contrast agent, and n ranges from 1 to 32 when the subject has received the dose of the MRI contrast agent;
(b) generate a readout of the (readout, $\alpha$)n module using a radial k-space trajectory; and
(c) reconstruct an MR angiogram of the subject from the MR data.

18. The system of claim 17 wherein the rate greater than 20 Hz ranges from 50 to 100 Hz.

19. The system of claim 17 wherein the radial k-space trajectory comprises radial views that are distributed across an azimuthal angle of at least 540 degrees.

20. The system of claim 17 wherein an offset frequency is varied across the radial views.

21. The system of claim 17 wherein a phase of $\alpha$ RF pulses and $\alpha/2$ RF pulses in the first and second $\alpha/2$ modules and the (readout, $\alpha$)n module alternate.

22. The system of claim 17 wherein the spoiler gradient module is integrated with one of the first or second $\alpha/2$ module or the (readout, $\alpha$)n module.

23. The system of claim 17 wherein the MR data is at least one of two-dimensional (2D) MR data, three-dimensional (3D) data, or cine MR data.

24. The system of claim 17 wherein the MR angiogram includes bright vascular signal.

25. The system of claim 17 wherein the set of modules forms a readout for a time-of-flight pulse MR angiography or a quiescent interval steady-state (QISS) angiography pulse sequence.

26. The system of claim 17 wherein the gradient-echo pulse sequence further includes a magnetization preparation module including a spatial saturation, spatial modulation of magnetization (SPAMM), fat suppression, diffusion, or magnetization transfer module.

27. The system of claim 17 wherein the pulse sequence is accelerated using radial undersampling, compressed sensing, or simultaneous multi-slice techniques.

28. The system of claim 17 wherein acquiring the MR data further includes synchronizing acquisition to a cardiac cycle or a respiratory cycle.

29. The system of claim 17 wherein acquiring the MR data further includes performing a motion reduction technique including navigator gating.

30. The system of claim 17 wherein the gradient-echo pulse sequence is performed before, during, or after the injection of the dose of the MM contrast agent.

31. The system of claim 17 wherein acquiring the MR data further includes performing a motion correction technique to align a plurality of sequentially acquired images.

32. The system of claim 17 wherein the computer system is further programmed to reduce signal intensity of background tissues by acquiring at least two sets of MR data using at least a first magnetization preparation module and a second magnetization preparation module, and computing a difference between the at least two sets of MR data.

33. A method for controlling a magnetic resonance imaging (MRI) system to create magnetic resonance (MR) angiograms of a subject, the method including steps comprising:
(a) controlling the MRI system to acquire MR data by performing a gradient-echo pulse sequence at a rate greater than 20 Hz when the subject is free of any MRI contrast agent, and at a rate greater than 10 Hz when the subject has received a dose of the MM contrast agent, the gradient-echo pulse sequence including at least one set of modules formed by a first $\alpha/2$ module, a (readout, $\alpha$)n module, a second $\alpha/2$ module, and a spoiler gradient module, wherein $\alpha$ denotes a radiofrequency (RF) flip angle, and n denotes a number of times that the set of modules is repeated;
(b) performing a readout using the (readout, $\alpha$)n module and a radial k-space trajectory;
(c) reconstructing an MR angiogram of the subject from the MR data.

34. The method of claim 33 wherein n ranges from 1 to 10 when the subject is free of the MRI contrast agent.

35. The method of claim 33 wherein n ranges from 1 to 32 when the subject has received the dose of the MRI contrast agent.

* * * * *

UNITED STATES PATENT AND TRADEMARK OFFICE
CERTIFICATE OF CORRECTION

Page 1 of 1

PATENT NO. : 10,845,447 B2
APPLICATION NO. : 16/040730
DATED : November 24, 2020
INVENTOR(S) : Robert R. Edelman et al.

It is certified that error appears in the above-identified patent and that said Letters Patent is hereby corrected as shown below:

In the Specification

Column 3, Line 2, "SSFP" should be --S5FP--.

Column 3, Line 6, "SSFP" should be --S5FP--.

Column 3, Line 18, "SSFP" should be --S5FP--.

In the Claims

Column 12, Claim 1, Line 5, "MM" should be --MRI--.

Column 12, Claim 17, Line 66, "MM" should be --MRI--.

Column 13, Claim 17, Line 3, "MM" should be --MRI--.

Column 13, Claim 17, Line 10, "MM" should be --MRI--.

Column 13, Claim 17, Line 13, "MM" should be --MRI--.

Column 13, Claim 17, Line 22, "MM" should be --MRI--.

Column 14, Claim 30, Line 17, "MM" should be --MRI--.

Column 14, Claim 33, Line 34, "MM" should be --MRI--.

Signed and Sealed this
Twenty-sixth Day of January, 2021

Drew Hirshfeld
*Performing the Functions and Duties of the
Under Secretary of Commerce for Intellectual Property and
Director of the United States Patent and Trademark Office*